(12) United States Patent
Roorda (10) Patent No.: US 8,815,278 B2
(45) Date of Patent: Aug. 26, 2014

(54) DRUG DELIVERY DEVICE AND METHOD

(75) Inventor: Wouter E. Roorda, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/186,259

(22) Filed: Jul. 19, 2011

(65) Prior Publication Data

US 2013/0023813 A1  Jan. 24, 2013

(51) Int. Cl.
*A61F 2/00* (2006.01)
*A61M 5/00* (2006.01)
*A61M 5/142* (2006.01)
*A61M 39/02* (2006.01)
*A61M 1/36* (2006.01)

(52) U.S. Cl.
CPC ......... *A61M 5/14276* (2013.01); *A61M 1/3655* (2013.01); *A61M 39/0208* (2013.01)
USPC .............................................. 424/424; 604/8

(58) Field of Classification Search
USPC ........ 604/8, 294, 9, 507, 93.01, 890.1, 891.1, 604/892.1; 623/1.14; 424/424
See application file for complete search history.

(56) References Cited

U.S. PATENT DOCUMENTS

| 3,797,485 | A | * | 3/1974 | Urquhart | 604/288.04 |
|---|---|---|---|---|---|
| 5,399,352 | A | * | 3/1995 | Hanson | 424/423 |
| 6,329,386 | B1 | | 12/2001 | Mollison | |
| 2005/0273033 | A1 | * | 12/2005 | Grahn et al. | 604/9 |
| 2006/0217798 | A1 | * | 9/2006 | Santini et al. | 623/1.42 |
| 2006/0224100 | A1 | * | 10/2006 | Gertner | 604/7 |
| 2008/0046073 | A1 | * | 2/2008 | Elshire | 623/1.36 |
| 2009/0192493 | A1 | * | 7/2009 | Meng et al. | 604/513 |
| 2009/0306595 | A1 | * | 12/2009 | Shih et al. | 604/151 |
| 2010/0010621 | A1 | * | 1/2010 | Klocke | 623/1.16 |
| 2010/0255061 | A1 | * | 10/2010 | de Juan et al. | 424/427 |
| 2010/0262215 | A1 | * | 10/2010 | Gertner | 623/1.1 |
| 2011/0066227 | A1 | * | 3/2011 | Meyer et al. | 623/1.42 |

* cited by examiner

*Primary Examiner* — Melanie Hand
(74) *Attorney, Agent, or Firm* — Blakely, Sokoloff, Taylor & Zafman LLP (57) ABSTRACT

Many people need vascular access for procedures such as hemodialysis. It is desirable that this access remain open or patent for the entire duration of the course of treatments. A drug delivery device and methods of using the device are introduced that delivery drug to venous anastomosis of a synthetic vascular access shunt. In some embodiments this device serves as the shunt connecting the target artery and vein to create the vascular access shunt.

18 Claims, 9 Drawing Sheets

DRUG DELIVERY DEVICE AND METHOD

BACKGROUND

Vascular access is important for the treatment of some chronic diseases such as those requiring hemodialysis treatments. A vascular access site should be prepared before starting those kinds of treatments because doing this allows for easier removal and replacement of the patient's blood during treatment. The access site should allow for continuous, high blood flow volumes. Common complications from vascular access sites include infection and low blood flow because the access passageway has clotted.

Arteriovenous (AV) fistulas or AV shunts are basic kinds of vascular access for hemodialysis. An AV fistula connects an artery to a vein in a patient (such as in the patient's forearm) and is useful because it causes the vein to grow larger and stronger allowing easier access to the blood system. The AV fistula is considered the best long-term vascular access for hemodialysis because it provides adequate blood flow, lasts a long time, and has a lower complication rate than other types of access. If an AV fistula cannot be created, an AV shunt or venous catheter may be needed.

An AV fistula requires planning because it takes time after surgery to develop—usually several months. But properly formed fistulas are less likely to form clots or become infected than are other access methods. Also, properly formed fistulas may work longer than other kinds of access—sometimes for years.

A synthetic arteriovenous shunt is another type of vascular access is. It connects an artery to a vein using a synthetic tube, or shunt, implanted in the patient's forearm, for example. The shunt becomes an artificial vein that can repeatedly receive a needle for blood access during hemodialysis. A shunt can be used sooner, 2 or 3 weeks after placement, than an AV fistula.

Compared with properly formed fistulas, shunts have more clotting and infection problems and need more frequent replacement.

Both types of access typically fail by clotting, which almost always starts with hyperplasia of the vessel wall near the venous anastomosis. What is needed is a convenient way to deliver a drug to that region without interfering with the function of the vascular access.

SUMMARY

Invention drug delivery devices are useful for delivering a drug or drug solution from a drug reservoir through a vascular access shunt to a venous anastomosis of that vascular access shunt or vasculature downstream from, the vascular access shunt. In some embodiments, the device comprises regions of differing permeability: a more permeable region and a less permeable region. In some embodiments, the ratio of permeability of the high permeability region to the low permeability region ranges from 100:1 to 10:1, including any value between those ratios. In some embodiments, the more permeable region separates the drug reservoir from the vascular access shunt.

The more permeable region allows the drug to move from the drug reservoir to the vascular access shunt. In some embodiments, the drug reservoir is adapted to supply drugs, through the more permeable region, to the boundary layer of the laminarly flowing blood in the vascular access shunt.

The drug delivery devices of this invention also comprise an elongate portion with two ends that are adapted to connect to mammalian vasculature. These ends and the elongate portion compose the vascular access shunt portion of the drug delivery device.

In some embodiments, the vascular access shunt part of the drug delivery device comprises a region comprising a self-sealing material.

In some embodiments, the vascular access shunt or the drug reservoir comprises one or more of polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes, and epoxy resins.

In some cases, the more permeable part is adapted to deliver drug to a boundary layer formed by the flow of blood through the vascular access shunt near the venous anastomosis.

In some embodiments the drug is selected to treat hyperplasia in the vessel walls near the venous anastomosis of the vascular access shunt or to treat thrombosis or to interfere with the stenotic cascade in the vessels near the venous anastomosis of the vascular access shunt. Specifically, in some embodiments, the drug comprises any one or any combination of heparin, antiproliferatives, antineoplastics, anti-inflammatories, anti-platelets, anticoagulants, antifibrins, anti-thrombins, antimitotics, antibiotics, antiallergics, antioxidants, or their mixtures, or any prodrugs, metabolites, analogs, homologues, congeners, functional derivatives, structural derivatives, or salts of these.

The outer wall of the device may comprise a self-sealing material, which in some cases is adapted to allow replenishment of the reservoir. One way of replenishing drug in the drug reservoir is by directly injecting drug into the reservoir.

DETAILED DESCRIPTION

The following description of several embodiments describes non-limiting examples that further illustrate the invention. All titles of sections contained in this document, including those appearing above, are not to be construed as limitations on the invention; but they are provided to structure the illustrative description of the invention that is provided by the specification.

Unless defined otherwise, all technical and scientific terms used in this document mean what one skilled in the art to which the disclosed invention pertains commonly understands them to mean. The singular forms "a", "an", and "the" include plural referents unless the context clearly indicates otherwise. Thus, for example, reference to "a fluid" refers to one or more fluids, such as two or more fluids, three or more fluids, etc. When an aspect is said to include a list of components, the list is representative. If the component choice is specifically limited to the list, the disclosure will say so. Moreover, listing components acknowledges that embodiments exist for each of the components and any combination of the components including combinations that specifically exclude any one or any combination of the listed components. For example, "component A is chosen from A, B, or C" discloses embodiments with A, B, C, AB, AC, BC, and ABC. It also discloses (AB but not C), (AC but not B), and (BC but not A) as embodiments, for example. Combinations that one of ordinary skill in the art knows to be incompatible with each other or with the components' function in the invention are excluded from the invention, in some embodiments.

Figure 1:
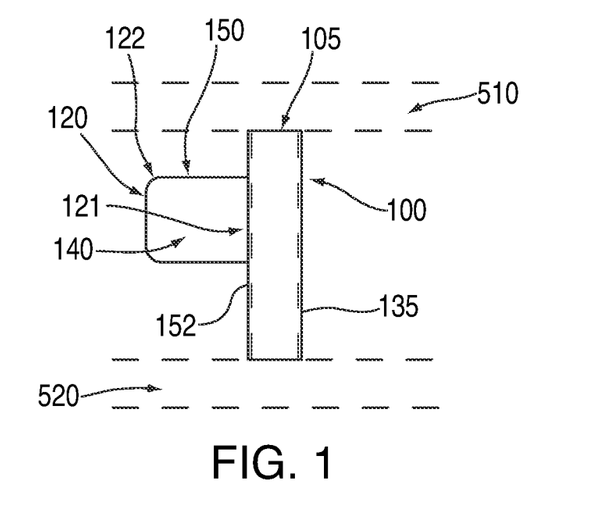
FIG. 1 depicts an embodiment of an invention drug delivery device.
Figure 2:
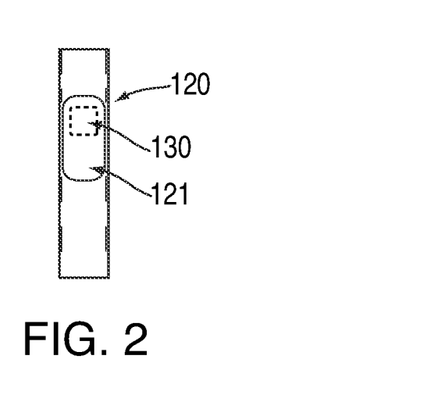
FIG. 2 depicts a side view of the device of FIG. 1.

FIG. 1 depicts the drug delivery device 100 according to an embodiment of the invention. Device 100 comprises a vascular access shunt 135 connected to a drug reservoir 150. An outer membrane or structure 120 encloses drug reservoir 150. The structure 120 comprises an internal region 121 consisting of the portion of structure 120 connected to vascular access shunt 135. The internal region 121 comprises more permeable region 130 that is disposed between drug reservoir 150 and vascular access shunt 135. In some embodiments, the entire internal region 121 comprises more permeable region 130. In other embodiments, as depicted in FIG. 2, only part of internal region 121 comprises more permeable region 130. The structure 120 also comprises an external region 122 consisting of the portion of structure 120 that is not connected to vascular access shunt 135. In general, external region 122 is less permeable than more permeable region 130. In some instances, external region 122 is referred to as a less permeable region.

FIG. 1 also shows artery 510 and vein 520 with phantom lines. When device 100 is implanted into a patient, it sits between artery 510 and vein 520, creating an alternative path for blood to travel from the heart through artery 510 and back to the heart through vein 520. This implantation creates an arteriovenous shunt.

As shown in FIG. 1, vascular access shunt 135 comprises two ends 105 for connecting artery 510 and vein 520 when the device 100 is implanted into the patient. These ends are adapted to connect to mammalian vasculature, which means that they have one or more of the following features:

- They are correctly sized to be connected to the target vasculature;
- They comprise material compatible with connecting to the target vasculature;
- They are correctly shaped to be connected to the target vasculature;
- They comprise material that can be sutured to the target vasculature; or
- They have any other feature that one of ordinary skill in the art would expect to provide the ability or improve on the ability to connect the ends 105 to the target vasculature.

Figure 4:
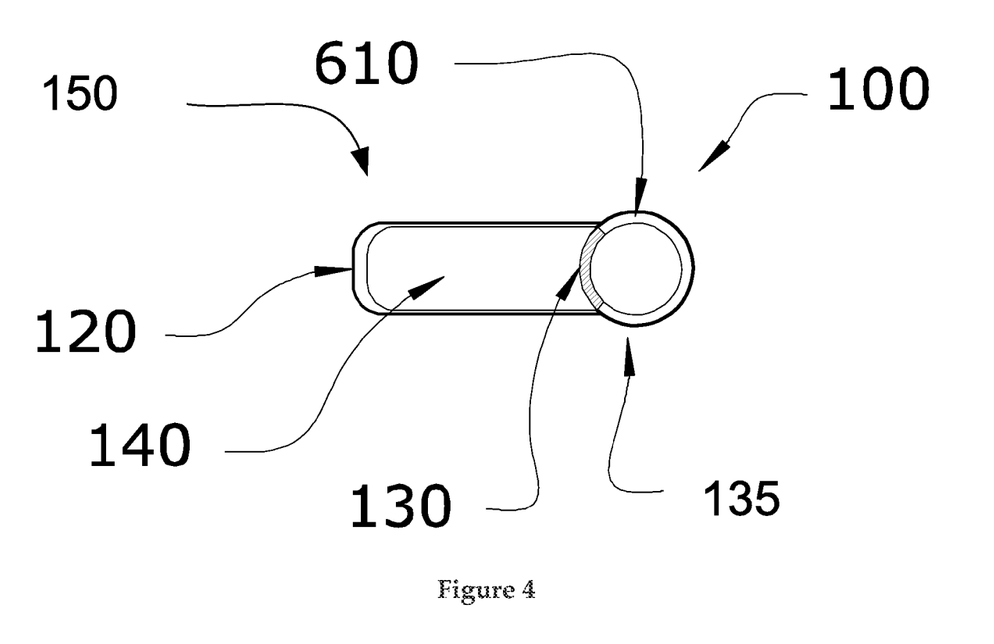
FIG. 4 depicts an expanded view of the device shown in cross-section.

In some embodiments, vascular access shunt 135 and drug delivery reservoir 150 are integral with one another or are a one-piece unit. For example, see FIG. 1. Drug delivery reservoir 150 connects to vascular access shunt 135. As seen in FIG. 1, ends 105 and external region 122 extend out away from vascular access shunt 135 substantially preventing any drug or drug solution contained in drug reservoir 140 from diffusing away from vascular access shunt 135. More permeable region 130 contacts wall 152 of vascular access shunt 135; this is also shown in FIG. 4.

In such embodiments, vascular access shunt 135 need not be more permeable to the drug or drug solution, in some embodiments, the more permeable portion of vascular access shunt 135 meets with more permeable region 130. In some embodiments, the composite device is constructed so that the more permeable portion of wall 152 and more permeable region 130 are the same structure.

Figure 3:
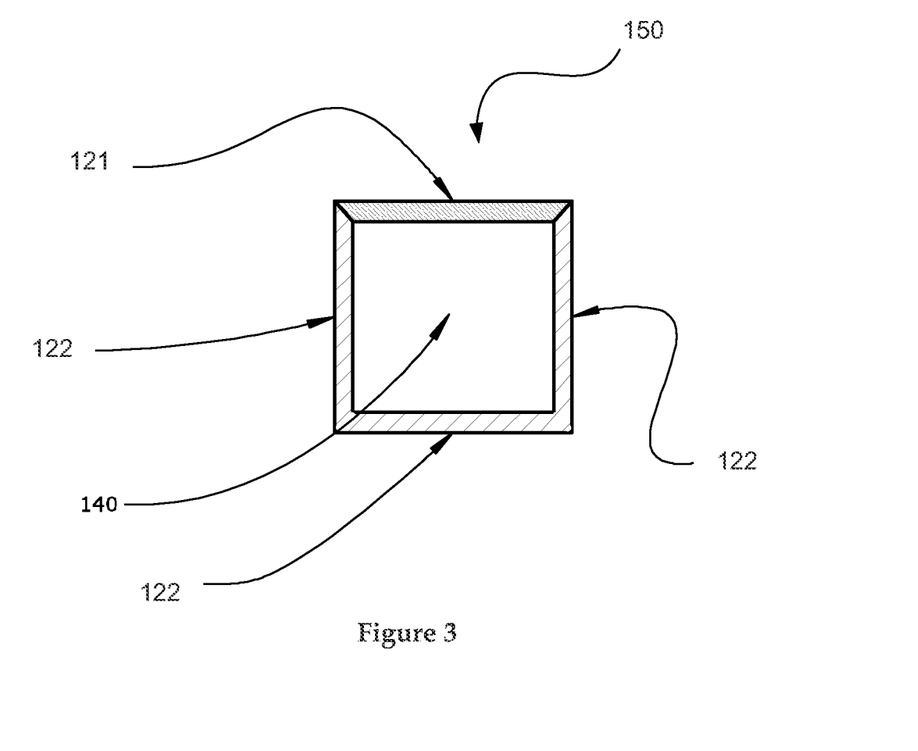
FIG. 3 depicts a cross-sectional view of an embodiment of an invention drug delivery reservoir.

FIG. 3 shows drug delivery reservoir 150 in cross-section. As depicted, drug delivery reservoir 150 has internal region 121 and an external region 122. As discussed above, internal region 121 is disposed between drug reservoir 150 and vascular access shunt 135, which is not shown in this figure. Drug reservoir 140 is the actual cavity within drug delivery reservoir 150 that contains the drug or drug solution.

While the embodiment in FIG. 3 is shown with a substantially rectilinear shape, the shape is not important to the function of drug delivery reservoir 150. Drug delivery reservoir 150 is sized appropriately to connect to vascular access shunt 135.

External region 122 is substantially less permeable to the drug or drug solution. In some embodiments, external region 122 is flexible, rigid, or semi-rigid. External region 122 may comprise a glass, polymer, rubber, ceramic, paper, cotton, or metal material. External region 122 can be monolithic, molded, pressed, or machined material or can comprise a woven substrate including a tightly woven substrate.

In some embodiments, more permeable region 130 is substantially more permeable than external region 122, or, in some embodiments, comprises a region with substantial permeability. In some embodiments, substantially more permeable means that more permeable region 130 allows diffusion from drug reservoir 140 at a rate within a range of rates such that neither too much or too little drug is delivered from device 100. In some embodiments, too much drug being delivered means that the amount of drug delivered causes the drug concentration to exceed the maximum therapeutic dosage. In some embodiments too much drug being delivered means that the amount of drug delivered causes the drug concentration to be high enough that the drug's toxic side effects substantially outweigh the drug's beneficial effects, as measured by an ordinarily skilled artisan. In some embodiments, too little drug being delivered means that the amount of drug delivered causes the drug concentration to fall below the minimum therapeutic dosage or to fall low enough that the drug does not cause any beneficial effect.

More permeable region 130 can be monolithic, woven, spun, etc. More permeable region 130 comprises a polymeric, rubber, glass, plastic, ceramic, or metallic material. Permeability can be achieved through any method known to those of ordinary skill in the art. For example, permeability can occur because of a physically open structure such as a microporous structure or permeability can occur because the material's chemical or physicochemical nature causes transport across the material. Or permeability can be achieved through other methods.

For drug delivery reservoir 150, both the materials composing the more permeable region and materials composing the less permeable regions can be selected largely independently of each other, provided that if one of the regions comprises a construction that substantially impedes penetration by a hypodermic needle or similar object, then the other region should be constructed such that the material allows penetration by a hypodermic needle or similar object. This exception applies to embodiments that are designed to be implanted and then later filled or refilled with additional drug solution using percutaneous access.

Device 100 should be susceptible to filling at the treatment facility if filling is not done at the manufacturing facility. This calls for some access to the drug reservoir. For instance, device 100 may have sides that can stand up to puncture by hypodermic needle and that can then reseal themselves after the needle's withdrawal. In some embodiments, the device may contain a valve that can open or close in response to pressure from a needle or catheter or other device. A Luer tip is suitable for some embodiments. Also, some device embodiments comprise a skin or subcutaneous access port. All of these accesses are well known to those of ordinary skill in the art and facilitate adding drug or drug solution to the device.

In some embodiments, the ability to refill the drug reservoir allows for a smaller device to be used because then the device need not contain enough drug or drug solution for the entire course of treatment. Moreover, after-implantation accessibility allows the physician to change the drug or drug combination should he or she decide to do so.

Both the more permeable and less permeable region materials should be compatible enough with each other so that they can be joined together. FIG. 4 depicts drug delivery device 100 in cross-section. Vascular access shunt 135 is attached to drug delivery reservoir 150 with more permeable region 130 disposed between drug delivery reservoir 150 and vascular access shunt 135. In this embodiment more permeable region 130 substitutes for part of wall 152 of vascular access shunt 135. In alternative embodiments more permeable region 130 connects directly to wall 152. In those embodiments, wall 152 should have substantial permeability to the drug or drug solution.

As above, FIG. 4 also depicts drug reservoir 140. Drug or drug solution travels from drug reservoir 140 through more permeable region 130, and, in some embodiments, wall 152, into the vascular access shunt 135.

Figure 5:
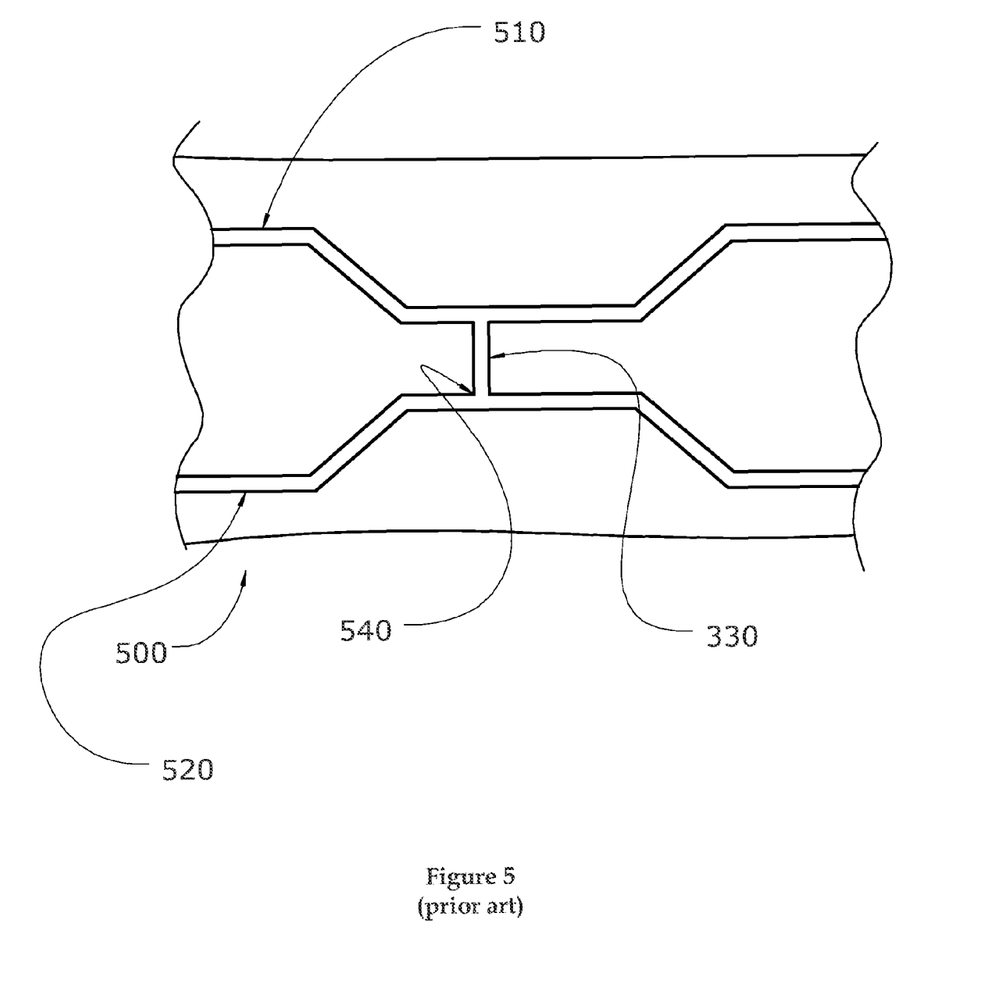
FIG. 5 is a schematic view of a prior art, synthetic vascular access shunt.

FIG. 5 depicts a schematic view of a portion of the patient. The patient's skin 500 is shown. Artery 510 carries blood away from the patient's heart, while vein 520 carries blood back to the heart. Shown between artery 510 and vein 520 is vascular access shunt 135. Vascular access shunt 135 connects to vein 520 at a downstream or venous anastomosis 540.

Figure 6:
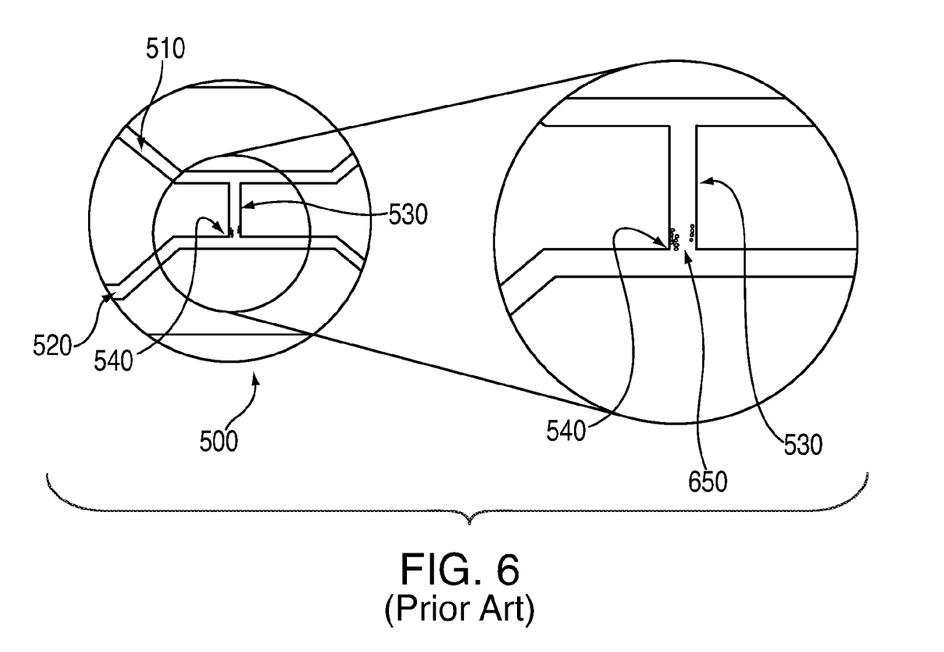
FIG. 6 is an expanded view of the anastomosis region of the prior art, synthetic vascular access shunt of FIG. 5.

FIG. 6 shows an expanded view of venous anastomosis 540 of FIG. 5. Fibromuscular hyperplasia of the vessel wall causes most stenosis problems, which is indicated on FIG. 6, as 650 at venous anastomosis 540.

Vascular access shunt 135 or drug reservoir 150 may comprise any biocompatible polymer or copolymer. Implantable medical devices may also be made of polymers that are biocompatible and biostable or biodegradable, the latter term including bioabsorbable and bioerodable.

As used in this document describing some embodiments, "biocompatible" refers to a polymer that is not toxic or has minimal toxicity; a polymer that does not injure living tissue or if it does injure living tissue, the injury is minimal and reparable; or does not invoke an immunological reaction in the tissue or if it does invoke an immunological reaction, the reaction is minimal and controllable. Also, the partially degraded polymer and all polymer degradation products have a biological interaction similar to the one I have described in this paragraph.

Among useful biocompatible, relatively biostable polymers are, without limitation, polyacrylates, polymethacrylates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Blends and copolymers of the above polymers may also be used and are within the scope of this invention. Based on these disclosures, those skilled in the art will recognize which implantable medical devices, and materials composing those devices, will be useful with this invention's embodiments.

"Polymer," "poly," and "polymeric" refer to materials resulting from a polymerization reaction and are inclusive of homopolymers and all forms of copolymers, "Copolymers" include random, alternating, block, and shunt variations. Also, those of ordinary skill in the art recognize that "terpolymer", or polymers made up of more than three different mers are a subset of copolymers.

Examples of biostable polymers include, among other polymers, polytetrafluoroethylene, fluorinated ethylenepropylene, polyvinylidene fluoride, polyether urethanes, polycarbonate urethanes, urethanes containing surface modifying additives where these additives provide silicone, hydrocarbon, polyethylene glycol, fluorocarbon or perfluorocarbon chains on the surface, polyurethanes with surface-modifying end groups consisting of silicone, hydrocarbon, polyethylene glycol or perfluoropolymer chains, polyolefins such as polyethylene and polypropylene, ethylene polymers such as ethylene vinyl acetate, ethylene coacrylic acid and ethylene covinyl alcohol, polyimide, polyetheretherketone, polyaryletherketone, polysulfone, PARYLENE, PARYLAST, polyethlyene teraphthalate, polyethylene oxide, polyurethane, silicones, polyesters, polyolefins, polyamides, polycaprolactam, polyvinyl chloride, polyvinyl methyl ether, polyvinyl alcohol, acrylic polymers and copolymers, polyacrylonitrile, polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), and any derivatives, analogs, homologues, salts, copolymers and combinations of these. In some embodiments, the polymers are selected such that they specifically exclude any one or any combination of any of the polymers taught in this document.

Any coatings of device 100 or device 100 itself may be composed of polymers. Representative examples of such polymers include, among other polymers, any one or any combination of fluorinated polymers or copolymers, e.g., poly(vinylidene fluorides), poly(vinylidene fluoride-co-hexafluoro propenes), poly(tetrafluoroethylenes), and expanded poly(tetrafluoroethylenes); poly(propylenes); co-poly(ether-esters); poly (ethylene oxides)/poly(lactic acids); poly (alkylene oxalates); poly(phosphazenes); poly(sulfones); poly(N-vinyl pyrrolidones); poly(ethylene oxides); poly(aminocarbonates); poly(iminocarbonates); poly(anhydride-co-imides); poly(hydroxyvalerates); poly(urethanes); vinyl halide polymers and copolymers, e.g., poly(vinyl chlorides); polyvinyl ethers e.g., polyvinyl methyl ethers); poly (acrylonitriles poly(vinyl ketones); silicones; poly esters); poly(olefins); copolymers of poly(isobutylenes); copolymers of ethylene-alphaolefins; poly(L-lactic acids); poly(L-lactides); poly(caprolactones); poly(lactide-co-glycolides); poly(hydroxybutyrates); poly(hydroxybutyrate-co-valerates); poly(dioxanones); poly(orthoesters); poly(anhydrides); poly(glycolic acids); poly(glycolides); poly(D,L-lactic acids); poly(D,L-lactides); poly(glycolic acid-co-trimethylene carbonates); poly(phosphoesters); poly(phosphoester urethanes); poly(vinyl aromatics), e.g., poly(styrenes); poly(lactides); poly(lactide-co-glycolide) copolymers; poly(vinyl esters), e.g., polyvinyl acetates; copolymers of vinyl monomers and olefins, e.g., poly(ethylene-co-vinyl alcohols) (EVALs); copolymers of acrylonitrile-styrenes; ABS resins; copolymers of ethylene-vinyl acetates; poi (trimethylene carbonates); poly(amides), e.g., Nylon 66 and poly(caprolactams); alkyd resins; poly(carbonates); poly(oxymethylenes); poly(imides); polyester amides); poly(ethers) including poly(alkylene glycols), e.g., poly(ethylene glycols) and polypropylene glycols); epoxy resins; polyurethanes; rayons; rayon-triacetates; biomolecules, e.g., fibrins; fibrinogens; starches; poly (amino acids); peptides; proteins; gelatins; chondroitin sulfates; dermatan sulfates (copolymers of D-glucuronic acids or L-iduronic acids and N-acetyl-D-galactosamines); collagens; hyaluronic acids; and glycosaminoglycans; poly(iminocarbonates); poly(ethylenes); other polysaccharides, e.g., poly(N-acetylglucosamines); chitins; chitosans; celluloses; cellulose acetates; cellulose butyrates; cellulose acetate butyrates; cellophanes; cellulose nitrates; cellulose propionates; cellulose ethers; carboxymethylcelluloses; or their derivatives, analogs, homologues, congeners, salts, or copolymers.

In these or other embodiments, the device further comprises a therapeutic agent. Throughout this disclosure, "drug", "therapeutic agent", and bioactive agent are used interchangeably unless the context clearly indicates otherwise. In some embodiments, the drug reservoir contains therapeutic or bioactive agents. The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis. The following types of therapeutic agents are found in some invention embodiments: proteins, peptides, antiproliferatives, antineoplastics, antiinflammatories, anti-plateletes, anticoagulants, antifibrins, antithrombins, antimitotics, antibiotics, antioxidants, antiallergics, or any prodrugs, metabolites, analogs, homologues, congeners, functional derivatives, structural derivatives, salts, or combinations of these. Some of the groups, subgroups, and individual bioactive agents may not be used in some embodiments of the present invention.

Any drug capable of treating, preventing, eliminating, or ameliorating hyperplasia is suitable for use in the practice of this invention. Likewise, any drug that prevents blood clotting is useful in the practice of this invention. Also, any drug capable of stopping, preventing, reversing, or slowing the stenotic cascade that results in stenosis of the autogenous or synthetic shunt is useful in the practice of this invention. Moreover, various invention embodiments exist that use any one or any combination of these drugs. Any of the drugs or drug combination of the previous paragraph can be combined or further combined with other drugs such as anti-proliferative drugs, anti-inflammatory drugs, pro healing drugs, or antithrombotic drugs.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic, or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, and ribozymes and retroviral vectors for use in gene therapy.

Antineoplastics or antimitotics include, for example, paclitaxel (TAXOL®, Bristol-Myers Squibb Co.), docetaxel (TAXOTERE®, Aventis S. A.), methotrexate, azathioprine, vincristine, vinblastine, fluorouracil, adriamycin, mutamycin, doxorubicin hydrochloride (ADRIAMYCIN®, Pfizer, Inc.) and mitomycin (MUTAMYCIN®, Bristol-Myers Squibb Co.), or any prodrugs, metabolites, analogs, homologues, congeners, functional derivatives, structural derivatives, salts, or combinations of these.

Antiplatelets, anticoagulants, antifibrin, and antithrombins include, for example, aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), or any prodrugs, metabolites, analogs, homologues, congeners, functional derivatives, structural derivatives, salts, or combinations of these.

Cytostatic or antiproliferative agents include, for example, actinomycin D, actinomycin IV, actinomycin I1, actinomycin X1, actinomycin C1, and dactinomycin (COSMEGEN®, Merck & Co., Inc. angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, or any prodrugs, metabolites, analogs, homologues, congeners, functional derivatives, structural derivatives, salts, or combinations of these.

Antiallergic agents include, but are not limited to, pemirolast potassium (ALAMAST®, Santen, Inc.), or any prodrugs, metabolites, analogs, homologues, congeners, functional derivatives, structural derivatives, salts, or combinations of these.

Examples of anti-inflammatory agents including steroidal and non-steroidal anti-inflammatory agents include tacrolimus, dexamethasone, clobetasol, or any prodrugs, metabolites, analogs, homologues, congeners, functional derivatives, structural derivatives, salts, or combinations of these.

Other bioactive agents useful in the present invention include, among other bioactive agents, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy) propyl-rapamycin; 40-O-[2-(2-hydroxy)ethoxy]- ethyl-rapamycin; tetrazole containing rapamycin analogs such as those described in U.S. Pat. No. 6,329,386; estradiol; clobetasol; idoxifen; tazarotene; alphainterferon; host cells such as epithelial cells; genetically engineered epithelial cells; dexamethasone; or any prodrugs, metabolites, analogs, homologues, congeners, functional derivatives, structural derivatives, salts, or combinations of these.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethylpiperidene-1-oxy, free radical (4-hydroxy-TEMPO), hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, functional derivatives, structural derivatives, salts, or combinations of these.

Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, functional derivatives, structural derivatives, salts, or combinations of these.

Other therapeutic substances or agents which may be appropriate include imatinib mesylate, pimecrolimus, and midostaurin.

Other therapeutic substances or agents which may be appropriate include alpha-interferon, bioactive RGD, and genetically engineered epithelial cells.

The foregoing substances can also be used in the form of prodrugs or co-drugs thereof. The foregoing substances are listed by way of example and are not meant to be limiting. Other active agents which are currently available or that may be developed in the future are equally applicable.

Dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the administered ingredient resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Ultimately, the physician determines what drug or drug combination, what dosage, what delivery rate, etc. for treatments using invention delivery devices. The dosage and delivery are linked in some embodiments. Also, these parameters influence the frequency the device will need to be refilled. Higher diffusion out of the drug reservoir may suggest more frequent replenishment.

In some embodiments, the diffusion rate is controlled by the permeability of more permeable region 130. Control over the permeability of more permeable region 130 to the chosen drug can control the rate of diffusion out of the drug reservoir 150 across the more permeable region 130.

Permeability can be controlled by a variety of methods. In some embodiments, permeability is controlled by mechanical means. All other things being equal, a thicker layer of a particular material yields a longer dwell time before drug delivery begins and a slower overall diffusion rate. Similarly mechanically, larger holes or passageways in the permeable membrane correlate with faster diffusion out of the device across the membrane.

In some embodiments, the permeability of the membrane is controlled chemically. Hydrophobic polymer membranes correlate with slower diffusion by hydrophilic drugs and faster diffusion by hydrophobic drugs. In a related manner, hydrogel or hydrophilic polymer membranes correlate with faster diffusion by hydrophilic drugs and slower diffusion by hydrophobic drugs.

Some embodiments use multiple strategies to control the drug diffusion rate. For instance, if the drug comprises microparticles, the diffusion of the microparticle out of the drug reservoir largely correlates with the nature of the microparticle, such as the size of the microparticle. Once the microparticle diffuses out of the drug reservoir, the rate of drug diffusion out of or off of the microparticle comes into play. Thus, selection of a microparticle-based drug gives two or more degrees of control over the diffusion rate.

Finally, permeability can be altered simply by choosing a different membrane material having a lower or higher permeability, as desired.

In some embodiments, the exit region of the more permeable portion of the device is from 0-1 inch; 0-0.5 inch; or 0-0.125 inch away from the anastomosis.

As delivered, the drug diffuses through more permeable region 130 and into vascular access shunt 135.

in some embodiments, drug delivery reservoir 150 is affixed to the outer wall of the shunt with an adhesive. The adhesive is any adhesive as one of ordinary skill would recognize as useful in such an application.

Many factors go into designing an implantable medical device that is suitable for implantation to form a vascular access shunt. These factors are well-known to ordinarily skilled artisans. Moreover, sometimes these factors are contradictory or improvement to one factor yields erosion of other factors making a balance between the factors necessary. An ordinarily skilled artisan that makes a determination of the material and form of an implantable medical device necessarily balances those factors. Making such a balance, in such a determination of the material and form for a device of the current invention by an ordinarily skilled artisan is referred to as adapting the device for implantation to form a vascular access shunt. A device designed in this manner is said to be adapted for implantation to form a vascular access shunt.

In some embodiments, "adapted for implantation to form a vascular access shunt" means that one or more of the following adaptations have been provided to or purposely chosen for the device:

The device comprises a material that provides an acceptably low level of foreign body response;

The device comprises a shape that arranges or fixes the more permeable region of the device in relation to the vascular access shunt to cause drug diffusion that is directional towards the vascular access shunt or highly directional towards the vascular access shunt (highly directional means 2-, 4-, 6-, 8-fold or greater diffusion in one direction as compared to the opposite direction);

The device comprises a drug reservoir accessible from outside of the patient (for example, accessible to a filling device);

The device comprises a skin port connected to, in communication with, or in fluid communication with a drug reservoir;

The device comprises a material strong enough to protect the drug reservoir;

The device comprises a material that improves the biocompatibility of the device with the internal body environment;

The device comprises a coating that improves the biocompatibility of the device with the internal body environment;

The device comprises a biocompatible material;

The device comprises a biocompatible polymer;

The device takes a shape to correctly sit or between the vessels that are or are to be shunted together;

The device comprises a large enough drug reservoir to hold enough drug such that one of ordinary skill in the art would consider the use of the device worthwhile;

The device comprises a drug reservoir that is capable of holding greater than a 3, 2, or 1 week drug supply;

The device comprises a drug reservoir that is capable of holding greater than a 1-7 days of drug supply;

The device comprises a structure that allows the device to remain or to be anchored substantially stationary within the body;

The device comprises a material that furnishes the device the ability to withstand being filled or refilled;

The device comprises a material that furnishes the device the ability to withstand being handling or to withstand implantation into the body;

The device comprises a high permeability region in which the permeability remains high enough for drug delivery or elution for the length of time the device remains within the body;

The device comprises a material that allows penetration of or connection with a filling device (for example, a hypodermic needle) that substantially seals itself after removal of the filling device;

The device is constructed out of expanded polytetrafluoroethylene;

or

The device comprises a material substantially free of undesirable materials or substantially free of undesirable, elutable materials.

Figure 7:
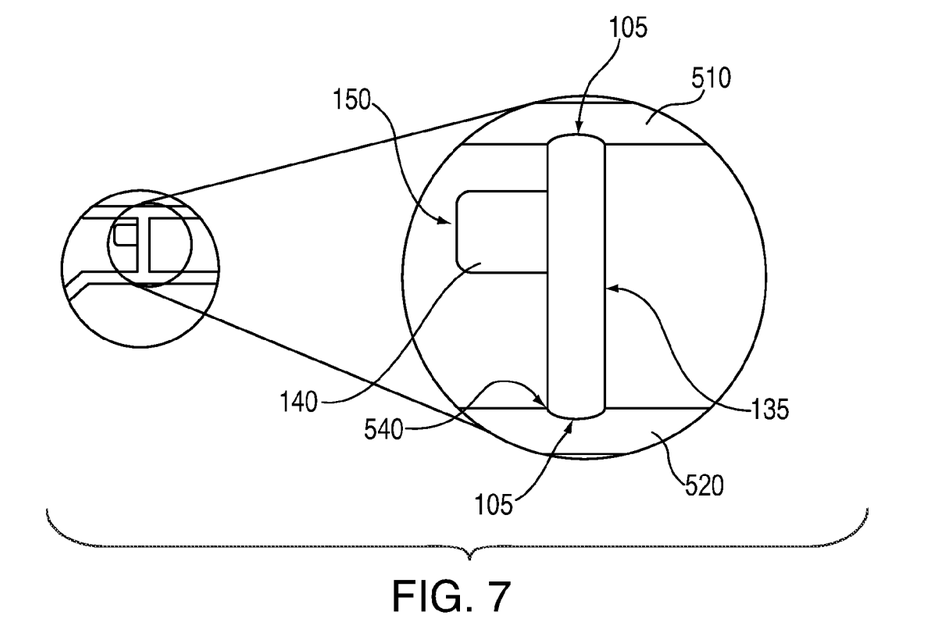
FIG. 7 depicts an embodiment of an invention device shown placed on the schematic view of FIG. 5.

FIG. 7 shows an invention drug delivery device 100 implanted as a vascular access shunt 135. Vascular access shunt 135 connects to artery 510 and vein 520 through ends 105. The figure depicts venous anastomosis 540 connecting between end 105 on the venous side of vascular access shunt 135 and vein 520. As shown, drug delivery reservoir 150 lies near the arterial side of vascular access shunt 135. As drug moves out of drug reservoir 140, it enters vascular access shunt 135 and flows toward venous anastomosis 540. Once in the vicinity of venous anastomosis 540, the drug treats the vascular tissue.

Drug Delivery

Since the drug enters into vascular access shunt 135 through its walls, the drug enters the boundary layer naturally set up by laminar blood flow within the shunt. Within the boundary layer, the drug retains a relatively high concentration because in laminar flow conditions little mixing of the fluid occurs as it flows through the conduit. As it moves downstream, the drug does not mix with blood for a time, allowing the drug to remain at a therapeutically significant concentration until the drug reaches downstream or venous anastomosis 540. Therefore, those treating the patient can select the drug to impede stenosis of venous anastomosis 540, and the drug can be delivered to the anastomosis without delivery substantially interfering with the shunt.

In some embodiments, the drug can be selected to treat thrombosis or to treat fibromuscular hyperplasia or to otherwise interfere with the stenotic cascade before stenosis occludes the venous anastomosis and renders useless vascular access shunt 135.

Drug delivery reservoir 150 is constructed such that more permeable region 130 contacts the wall of vascular access shunt 135, at least in part. The goal is to have drug diffuse out of drug reservoir 140 through more permeable region 130 and through the wall of vascular access shunt 135. As the drug diffuses through the shunt wall into the boundary layer within the shunt, it ultimately arrives at venous anastomosis 540. Therefore, the arrangement of external region 122 and more permeable region 130 should accentuate the directionality of the diffusion from drug reservoir 140.

In some embodiments drug reservoir 140 is adapted to supply drug through the more permeable region 130 to the boundary layer of laminarly flowing blood in the vascular access shunt 135. In some embodiments adapted to supply drug through the more permeable region 130 to the boundary layer of laminarly flowing blood in the vascular access shunt 135 means having any structure or property that one of ordinary skill in the art would expect the cause the device to be better able to supply drug to the laminarly flowing blood in venous access shunt 135, such as:

The material of the drug reservoir 140 that context the drug or drug solution is compatible with the drug or drug solution;

The drug reservoir 140 contains no or fewer interior barriers to the flow of drug or drug solution;

The drug reservoir 140 is substantially impermeable to drug or drug solution except at more permeable regions;

The drug delivery device 100 is substantially stable to chemical or physical attack by the environment of the body;

The drug reservoir 140 can be refilled without substantially affecting the structural integrity of drug delivery device 100;

The drug delivery device 100 is substantially impermeable to fluids or materials of the environment of the body; or Any other feature or change that one of ordinary skill in the art would make or incorporate into the device to improve the device's ability to supply drug.

Use of the device can be further understood by referencing the following methods.

Figure 8:
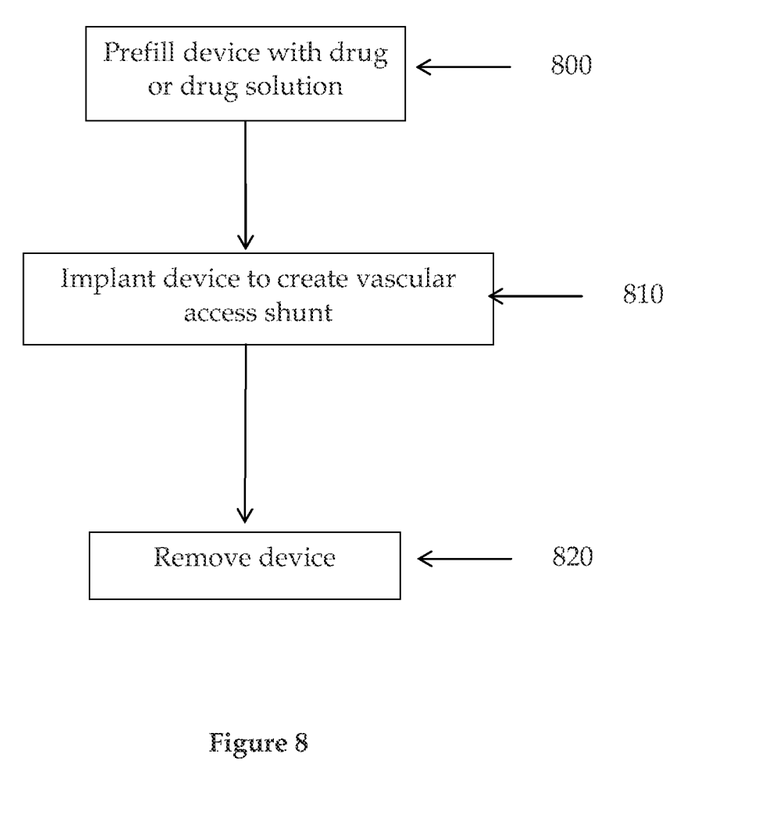
FIG. 8 depicts a method of delivering drug to a venous anastomosis using an embodiment of a drug delivery device of this invention wherein the method includes a pre-filling step.

FIG. 8 depicts an embodiment of a method of delivering a drug to venous anastomosis 540 with pre-filling step 800 comprising filling device 100 with a drug or drug-containing solution. In some embodiments, this filling occurs by inserting a hypodermic needle into drug reservoir 140. The outer part of device 100 should be constructed of a material that allows only minimal leakage through the hypodermic needle penetration point once the needle has been withdrawn. In that sense, the material through which the needle passes during this filling step is self-sealing. The method also comprises implanting step 810 comprising implanting device 100 to form a vascular access shunt 135 after the device has been filed. Some embodiments of these methods have removing step 820 comprising removing device 100 from the patient when drug reservoir 140 is empty or when the patient no longer needs device 100.

Figure 9:
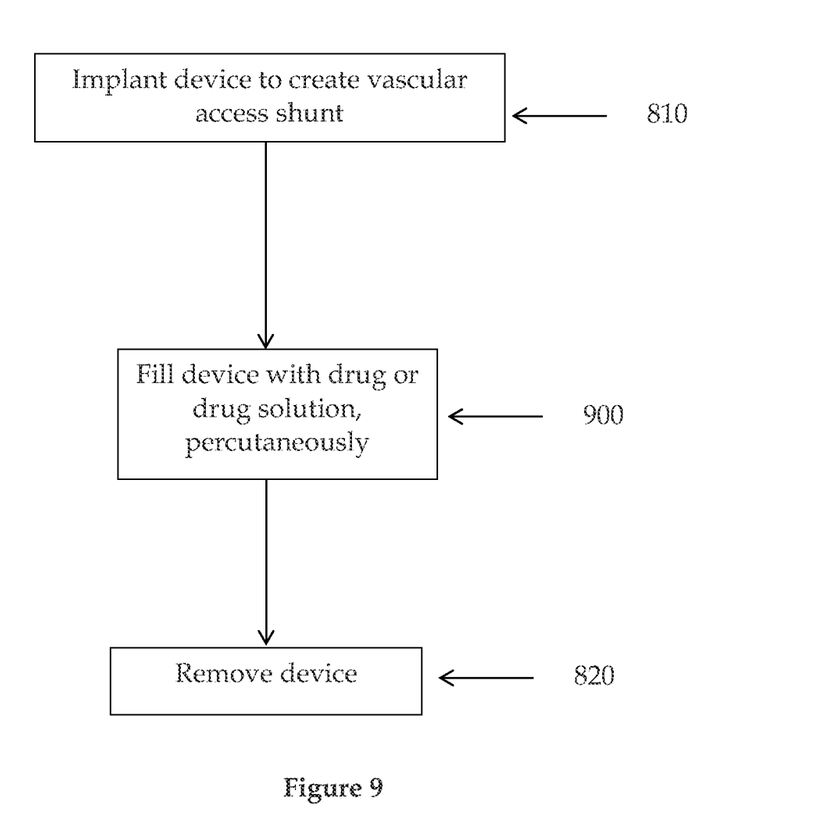
FIG. 9 depicts a method of delivering drug to a venous anastomosis using an embodiment of a drug delivery device of this invention wherein the method includes a percutaneous filling step.

FIG. 9 depicts an embodiment of a method of delivering a drug to venous anastomosis 540 comprising implanting step 810 comprising implanting device 100 to form a vascular access shunt 135 before device 100 has been filed. This step is followed by percutaneous-filling step 900 comprising filling device 100 with a drug or drug-containing solution after device 100 has been implanted. In some embodiments, percutaneous-filling step 900 comprises inserting a hypodermic needle through the patient's skin into drug reservoir 140 and operating the attached syringe to deposit drug or drug solution into drug reservoir 140. Some embodiments of these methods have removing step 820 comprising removing device 100 from the patient when drug reservoir 140 is empty or when the patient no longer needs the device.

Figure 10:
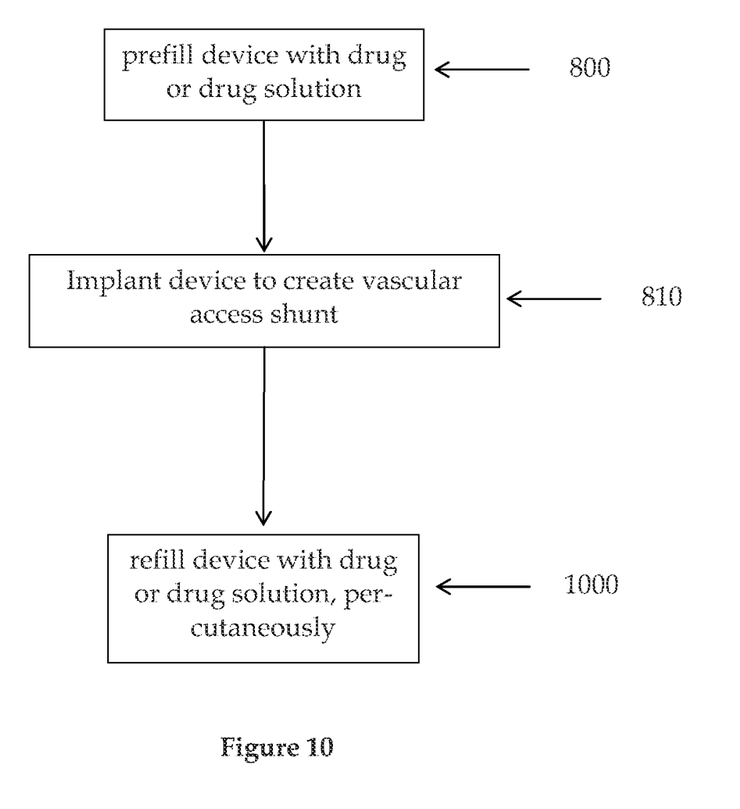
FIG. 10 depicts a method of delivering drug to a venous anastomosis using an embodiment of a drug delivery device of this invention wherein the method includes a pre-filling step and a percutaneous filling step.

FIG. 10 depicts an embodiment of a method of delivering a drug to vascular access shunt 135 with prefilling step 800 comprising filling device 100 with a drug or drug-containing solution. The method also comprises implanting step 810 comprising implanting device 100 to form a vascular access shunt 135 after the device has been filed. Some embodiments of these methods have refilling step 1000 comprising refilling device 100 when drug reservoir 140 is depleted. In some embodiments, refilling step 1000 comprises inserting a hypodermic needle through the patient's skin into drug reservoir 140 and operating an attached syringe to deposit drug or drug solution into drug reservoir 140. Other embodiments use other methods of refilling the drug similar to using a hypodermic needle and syringe couple.

Figure 11:
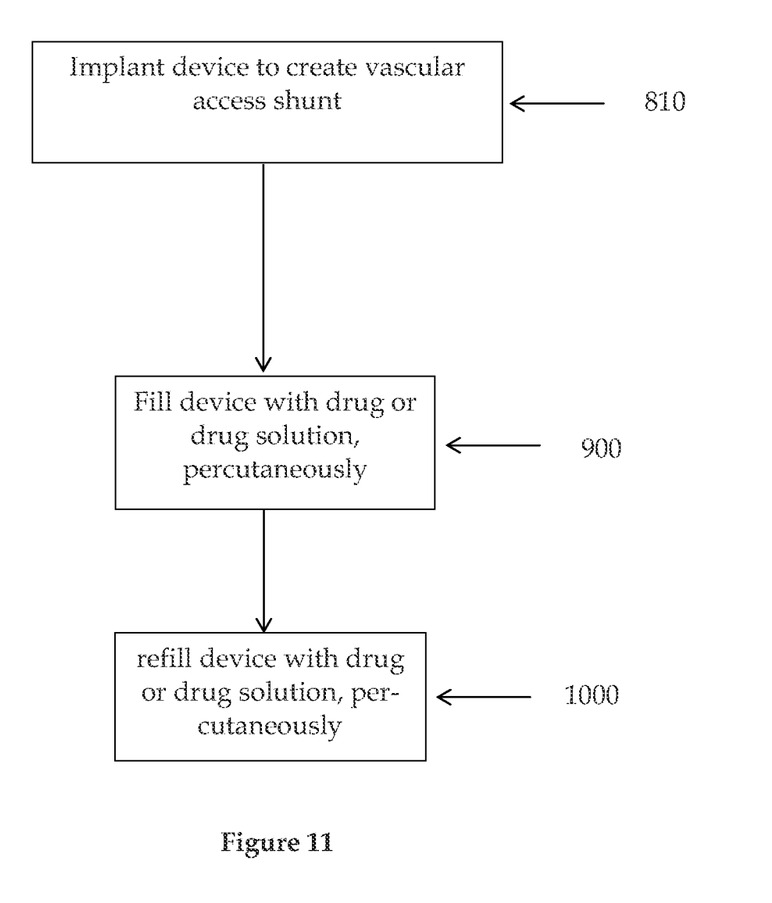
FIG. 11 depicts an alternative method of delivering drug to a venous anastomosis using an embodiment of a drug delivery device of this invention wherein the method includes two percutaneous filling steps a filling step and a refilling step.

FIG. 11 depicts an embodiment of a method of delivering a drug to venous anastomosis 540 comprising implanting step 810 comprising implanting device 100 to form a vascular access shunt 135 before device 100 has been filed. This step is followed by percutaneous-filling step 900 comprising filling device 100 with a drug or drug-containing solution after device 100 has been implanted. In some embodiments, percutaneous-filling step 900 comprises inserting a hypodermic needle through the patient's skin into drug reservoir 140 and operating the attached syringe to deposit drug or drug solution into drug reservoir 140. Other methods of filling the drug similar to using a hypodermic needle are used by other invention embodiments. Some embodiments of these methods have refilling step 1000 comprising refilling device 100 when drug reservoir 140 is depleted. In some embodiments, refilling step 1000 comprises inserting a hypodermic needle through the patient's skin into drug reservoir 140 and operating the attached syringe to deposit drug or drug solution into drug reservoir 140. Other embodiments use other methods of refilling the drug similar to using a hypodermic needle and syringe couple.

In addition to refilling drug reservoir 140 as described above, other embodiments exist that use other types of drug or drug solution replenishment. For example, the reservoir may comprise a Luer-type fitting for mating with a corresponding Luer-type fitting on a replenishment device.

As discussed elsewhere in this document, filling can occur either before implantation or after implantation. When filling occurs before implantation, filling can be immediately before implantation, such as within 0 to 360 minutes before implantation. In some embodiments, the drug reservoir is filled with drug before the device is shipped from the manufacturing facility. But filling this long before use raises a drug stability problem that can diminish the expected shelf life of the device. While this problem is not insurmountable, it can be avoided by filling the device near the time the device is to be implanted. The device without any drug or drug solution has a much longer shelf life than an already filled device. Filling can also occur after the physician has implanted the device. When done at that time, filling can be very similar to refilling.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true, intended, explained, disclose, and understood scope and spirit of this invention's multitudinous embodiments and alternative descriptions.

Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

Finally, headings are for the convenience of the reader and do not alter the meaning or content of the disclosure or the scope of the claims.

What is claimed is:

1. A device comprising:
a vascular access shunt having a wall, an inner lumen, and two or more ends adapted to connect to mammalian vasculature, the wall having a substantially permeable region between an outer surface and the inner lumen; and
a structure having a reservoir enclosed between an external region and an inner membrane, wherein the structure is coupled with the outer surface such that the inner membrane covers the substantially permeable region, and wherein the inner membrane is more permeable than the external region to allow a drug disposed within the reservoir to move from the reservoir through the inner membrane and the substantially permeable region into the inner lumen.

2. The device of claim 1 wherein the reservoir contains the drug and is adapted to supply the drug through the inner membrane and the substantially permeable region to a boundary layer of laminarly flowing blood in the inner lumen.

3. The device of claim 2 wherein the drug treats hyperplasia at an anastomosis where one of the two or more ends connect to mammalian vasculature.

4. The device of claim 2, wherein the drug is one of heparin, antiproliferatives, antineoplastics, anti-inflammatories, antiplatelets, anticoagulants, antifibrins, antithrombins, antimitotics, antibiotics, antiallergics, antioxidants, or their mixtures, or any prodrugs, metabolites, analogs, homologues, congeners, functional derivatives, structural derivatives, salts, or combinations of these.

5. The device of claim 1 wherein the external region comprises a self-sealing material.

6. The device of claim 5 wherein the self-sealing material is adapted to allow replenishment of the reservoir.

7. The device of claim 6 wherein replenishment comprises injection of the drug into the reservoir.

8. The device of claim 1 wherein the vascular access shunt or the structure comprise one or more of polytetrafluoroethylene; fluorinated ethylenepropylene; polyvinylidene fluoride; polyether urethanes; polycarbonate urethanes; urethanes containing surface modifying additives wherein these additives provide silicone, hydrocarbon, polyethylene glycol, fluorocarbon or perfluorocarbon chains on the surface; polyurethanes with surface-modifying end groups consisting of silicone, hydrocarbon, polyethylene glycol or perfluoropolymer chains; polyolefins; polyethylene; polypropylene, ethylene polymers; ethylene vinyl acetate; ethylene coacrylic acid; ethylene covinyl alcohol; polyimide; polyetheretherketone; polyaryletherketone; polysulfone; PARYLENE; PARYLAST; polyethlyene terephthalate; polyethylene oxide; polyurethane; silicones; polyesters; polyolefins; polyamides; polycaprolactams; polyvinyl chloride; polyacrylates; polymethacrylates; polyureas; polyurethanes; polyvinylhalides; polyvinylidenehalides; polyvinylethers; polyvinylaromatics; polyvinylesters; alkyd resins; polysiloxanes; epoxy resins; polyvinyl methyl ether; polyvinyl alcohol; acrylic polymers and copolymers; polyacrylonitriles; polystyrene copolymers of vinyl monomers with olefins; styrene acrylonitrile copolymers; ethylene methyl methacrylate copolymers; ethylene vinyl acetate; polyethers; rayons; cellulosics; cellulose acetate; cellulose nitrate; cellulose propionate; or any derivatives, analogs, homologues, salts, copolymers or combinations of these.

9. The device of claim 1 wherein the ratio of the permeability of the inner membrane to the external region is 10:1 or 100:1.

10. The device of claim 3 wherein the external region includes a self-sealing material, wherein the self-sealing material is adapted to allow replenishment of the reservoir, wherein the drug is one of heparin, antiproliferatives, antineoplastics, anti-inflammatories, anti-platelets, anticoagulants, antifibrins, antithrombins, antimitotics, antibiotics, antiallergics, antioxidants, or their mixtures, or any prodrugs, metabolites, analogs, homologues, congeners, functional derivatives, structural derivatives, salts, or combinations of these, and wherein the ratio of the permeability of the inner membrane to the external region is 10:1 or 100:1.

11. The device of claim 3, wherein the drug includes a microparticle carrier, and wherein the microparticle carrier is sized to diffuse through the inner membrane at a rate such that the reservoir supplies the drug to the flowing blood for at least one week.

12. The device of claim 11, wherein the drug includes one of heparin, antiproliferatives, antineoplastics, anti-inflammatories, anti-platelets, anticoagulants, antifibrins, antithrombins, antimitotics, antibiotics, antiallergics, antioxidants, or their mixtures, or any prodrugs, metabolites, analogs, homologues, congeners, functional derivatives, structural derivatives, salts, or combinations of these.

13. The device of claim 1, wherein the inner membrane includes a polymer membrane.

14. The device of claim 13, wherein the polymer membrane includes a woven polymer.

15. The device of claim 13, wherein the polymer membrane includes a hydrophobic polymer.

16. The device of claim 13, wherein the polymer membrane includes a hydrophilic polymer.

17. The device of claim 7, wherein the self-sealing material includes a valve openable in response to pressure.

18. The device of claim 17, wherein the valve includes a luer-type fitting.

* * * * *